United States Patent [19]

Hermony et al.

[11] Patent Number: 5,554,848
[45] Date of Patent: Sep. 10, 1996

[54] GANTRY FOR NUCLEAR MEDICINE IMAGING SYSTEMS

[75] Inventors: Nathan Hermony; Dan Inbar; Moshe B. Porath; David Freundlich, all of Haifa, Israel

[73] Assignee: Elscint Ltd., Haifa, Israel

[21] Appl. No.: 166,897

[22] Filed: Dec. 15, 1993

Related U.S. Application Data

[63] Continuation of Ser. No. 785,056, Oct. 30, 1991, abandoned.

[30] Foreign Application Priority Data

Nov. 2, 1990 [IL] Israel ............................. 096230

[51] Int. Cl.⁶ ...................................... G01T 1/166
[52] U.S. Cl. ...................... 250/363.05; 250/363.04; 378/15
[58] Field of Search .................. 250/363.04, 363.05; 378/15

[56] References Cited

U.S. PATENT DOCUMENTS

| H12 | 1/1986 | Bennett et al. | 20/363.04 |
|---|---|---|---|
| 3,011,057 | 11/1961 | Anger . | |
| 3,970,853 | 7/1976 | Kuhl et al. | 250/363.04 |
| 4,216,381 | 8/1980 | Lange | 250/363.05 |
| 4,472,052 | 9/1984 | Löfgren | 378/15 |
| 4,503,331 | 3/1985 | Kovacs, Jr. et al. | 250/363.04 |
| 4,692,624 | 9/1987 | Ichihara | 250/363.04 |
| 4,698,506 | 10/1987 | Fujiki | 250/363.04 |
| 4,912,735 | 3/1990 | Beer | 378/15 |
| 4,982,416 | 1/1991 | Pare et al. | 378/209 |
| 5,057,692 | 10/1991 | Greskovich et al. | 250/363.04 |

FOREIGN PATENT DOCUMENTS

| 2007938 | 5/1979 | United Kingdom . |
|---|---|---|
| 2026812 | 2/1980 | United Kingdom . |
| 2061028 | 5/1981 | United Kingdom . |
| 8800025 | 1/1988 | WIPO . |

*Primary Examiner*—Carolyn E. Fields
*Attorney, Agent, or Firm*—Sandler, Greenblum & Bernstein

[57] ABSTRACT

A nuclear medicine diagnostic imaging system wherein the gamma camera rotates about the patient and is coupled to receive electrical power, control signals and to transmit data using cableless coupling means. This enables the system to provide whole body helical scans. Reconstruction begins during the first revolution of the camera about the patient and continues during subsequent revolutions to provide evolving images.

18 Claims, 2 Drawing Sheets

GANTRY FOR NUCLEAR MEDICINE IMAGING SYSTEMS

This application is a continuation of application Ser. No. 07/785,056, filed Oct. 30, 1991, now abandoned.

FIELD OF THE INVENTION

This invention relates to radiation imaging systems and in particular to systems for performing single photon emission computer tomography with a scintillation detector rotated in an orbit about a patient.

BACKGROUND OF THE INVENTION

In nuclear medicine diagnostic imaging a radionuclide is administered to a patient and a nuclear camera or gamma camera such as the Anger gamma camera shown in U.S. Pat. No. 3,011,057 is used to produce a visual image of the distribution of the radionuclide within the patient. The nuclear or gamma camera devices that detect the emitted radiation are used in conjunction with a collimator to selectively filter the passage of emitted radiation from the patient to the gamma camera. The gamma camera includes a scintillation crystal positioned behind the collimator. The crystal when struck by radiation scintillates or emits visible light. The visible light is detetected by transducers such as photomultipliers and translated into electrical signals.

When gamma cameras were first used for medical diagnostic imaging, they produced images of organs such as the brain and thyroid gland. Through the years there has been significant improvements in the cameras and new radioactive isotopes for ingestion by the patient have been developed. The improved cameras along with the new radioactive isotopes have been used for conducting whole body studies to detect cancer in the patient in such places as in the bone marrow. More recently, the gamma camera systems have been used to obtain tomographic images in studies known as emission computed tomography (ECT) or single photon emission computed tomography (SPECT).

These gamma camera systems are used to cause the gamma camera detector means to orbit the patient and acquire data during orbit. The data is then used with reconstruction algorithms to provide tomographic images of the portions of the patient orbitted.

The equipment for enabling the scintillation detector to orbit the patient comprise a stationary gantry having a rotor supporting the nuclear camera detector means during the rotation of the nuclear camera detector means about the patient. Originally, the detector means was rotated in a circular path. However, soon it became apparent that images with a greater resolution could be obtained if the path was modified so that the gamma camera was proximate to the patient during the entire orbit. Thus, the nuclear camera detector means and the rotating portion of the gantry were programmed and controlled to follow complicated orbital paths. A further improvement in the ECT systems comprised using more than one head; i.e., more than one nuclear camera detector on the rotating part of the gantry.

Up until now the rotatable nuclear gamma detector means was electrically coupled to the stationary portion of the ECT system by cable arrangements. For example, power for the special photomultiplier tube power supply is required. The special power supply was either mounted on the stationary portion of the gantry or on the rotating portion. In either case, power had to be supplied to the rotating portion of the gantry for among other things, powering the photomultipliers. Conventionally, the required power is transmitted to the rotating member via flexible power cables. Complicated cable arrangements are provided that enable sufficient play in the cables so that the rotating portion of the gantry can complete at least one rotation.

In addition to the power supplied to the rotating portion of the gantry, it is also necessary to supply control signals to the rotating portion of the gantry. The control signals are used in the control of such things as the locus of the path taken by the nuclear gamma camera detector means during its rotation about the patient.

Also, the data; i.e., the electrical signals provided by the photomultiplier tubes, for example, have to be supplied from the rotating portion of the gantry to the processing means which is removed, from the gantry.

In practice the cabling arrangements for transferring power, control signals and data to and from the rotating camera head are a constant source of maintenance problems. In addition, the cabling severely limits the rotation. Thus, in practice the gamma camera head can only be rotated through approximately one or two rotations. This limitation slows down the examinations significantly.

In addition, with the use of faster radionuclides the capability of rotating more than once is even more desirable. For example, normally the rotating head is brought through one rotation in a slow mode to assure that there is no interference problems between the rotating portions of the gantry and stationary portions of the system including the patient bed. With the present equipment it is necessary to return the rotor to the beginning of its rotation after the slow trial run by reversing the rotation step and then to once again rotate through the data acquisition arc while acquiring data. The necessity of reversing the rotation requires extra time. It would be much more efficient if it was possible to continue the rotation and acquire data rather than having to reverse the rotation to return to the starting position.

Another advantage is that the continuous rotation capability makes it possible to use multiple rotations with each rotation at a higher speed than presently used during acquisition whereby even though less data is acquired per rotation the plurality of rotations results in more data being acquired such that true motion correction in .real time can be obtained by the multiple rotation enabling multiple views from the same angular position. This makes it possible to accurately determine motion and, for example, to reject the data from one revolution out of many. It also enables averaging of the data and thus improves the signal-to-noise ratio and the uniformity of the slices. In the prior art "nearby" views were used in the motion correction algorithm, and true motion correction was not possible. With multiple rotations true motion correction even in real time is now possible.

A related feature of the inventive capability of performing repeated revolutions about the patient is the capability of more absolutely determining patient motion and of rejecting data obtained during a revolution when the patient motion was excessive.

Since faster and repeated revolutions about the patient are used during acquisition cycles, the necessity of half life time corrections for such isotopes as $^{13}I$, 99mTc and 20T are not needed. A related feature is that ultra short life isotopes which were previously not feasible for use are now useable.

Yet another feature of the present invention is the capability of performing whole body scans by having the camera head or heads follow a cylindrical helical locus about the patient by combining elliptical and longitudinal motions.

Yet another related feature of the present invention provides for an evolving image. The camera head or heads continuously revolve about the image, with each revolution requiring about 30 seconds. Image reconstruction starts shortly after the first half of the first revolution. The image evolves as the number of revolutions increases. The operator stops the acquisition when he is satisfied with the quality of the evolved image.

BRIEF DESCRIPTION OF THE INVENTION

Accordingly, in a preferred aspect of the present invention, a single photon emission computer tomography system is provided, said system comprising:

a stationary gantry member having a central axis, a rotatable nuclear camera detector means mounted on said gantry member for rotation about said central axis, patient support means aligned with said central axis to have said gamma camera means rotate about a patient on said patient support means, control and processing means for supplying control signals to said system, for receiving data acquired by said system responsive to said control signals and for processing said received data to provide tomographic images of said patient, and cableless coupling means for coupling electrical power, control signals and radioactive emission data between said rotatable gamma camera means and the stationary gantry member of the system.

According to a feature of the invention, the cableless coupling means comprises slip rings and associated components such as brushes for coupling the electrical power, the control signals and/or the data acquired during a scan process.

In accordance with another feature of the invention, the cableless coupling means comprises means for inductively coupling said rotating portion to said stationary gantry member for enabling the coupling of the control signals and radioactive emission data between the said stationary gantry member and said rotatable gamma camera means.

In accordance with yet another feature of the present invention, the cableless coupling means for coupling control signals and/or radioactive emission data between said static gantry member and rotatable gamma camera means comprises optical coupling means.

BRIEF DESCRIPTION OF THE DRAWINGS

The above and other objects and features of the present invention will be best understood when considered in the light of the following description of a preferred aspect of the present invention made in conjunction with the attached drawings; wherein.

GENERAL DESCRIPTION

Figure 1:
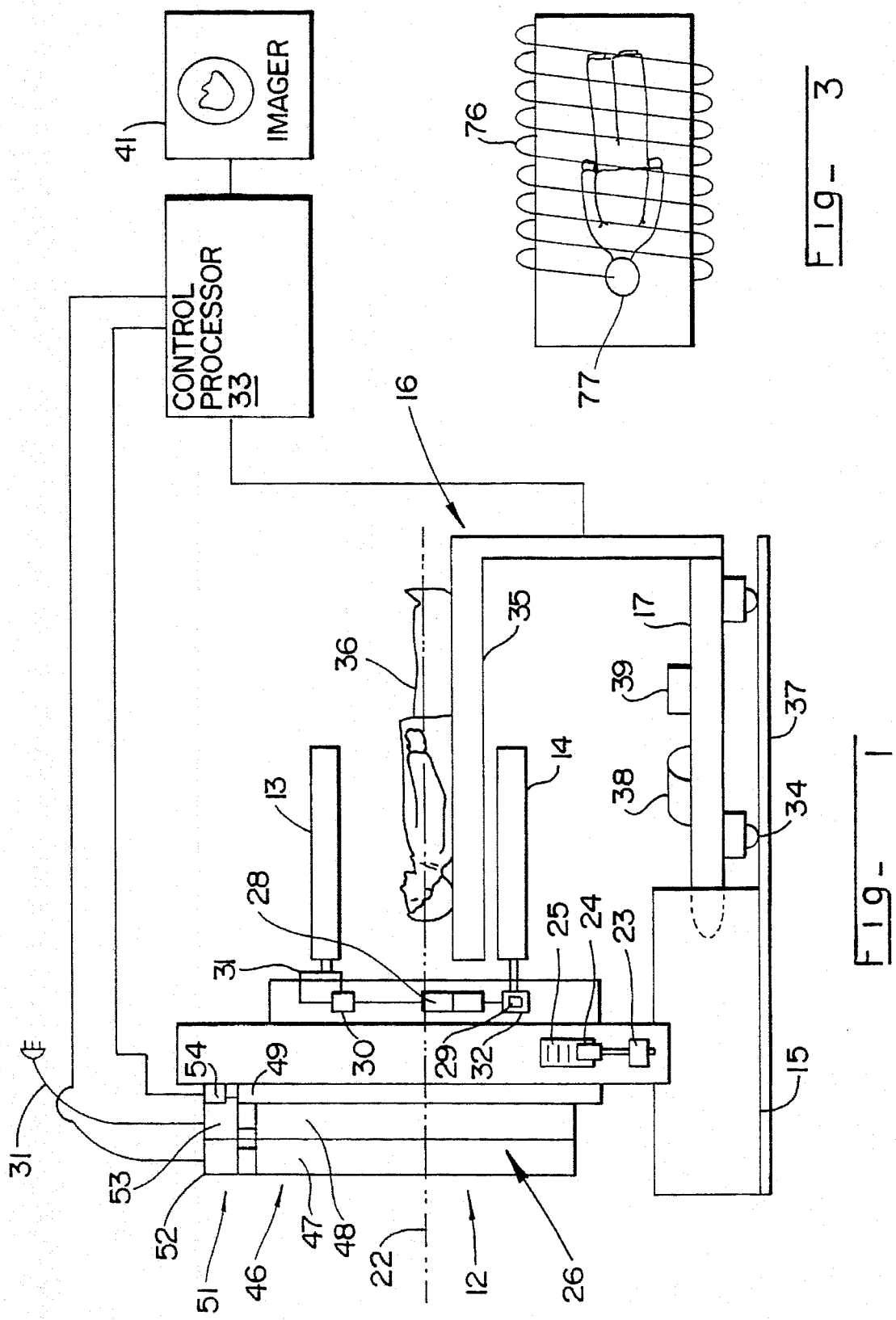
FIG. 1 is a schematic-block diagram showing of the ECT system of the invention.

The ECT system 11 of FIG. 1 includes a gantry 12 on which are mounted detector head means such as first detector head 13 and an oppositely disposed second detector head 14. The detector heads are mounted spaced apart from each other with room therebetween for the insertion of a patient table 16 mounted on its own mobile base 17. The gantry 12 includes a non-rotating gantry base 15. In the ECT system, means are provided for rotating a portion of the gantry about a central axis 22. The means are indicated in FIG. 1 by the motor 23 which rotates a gear head 24 that meshes with a gear 25 on the rotating portion 26 of the gantry to which the heads are attached. As the motor rotates the gears 24 and 25 cause the rotating portion of the gantry, which includes the heads 13 and 14, to rotate about the central axis of the system 22. While two detector heads are shown, it should be understood that three or more heads could also be used within the scope of the invention.

The patient 27 is generally aligned with the central axis 22. Means are normally provided so that the rotation orbit is controlled to cause the head means such as heads 13 and 14 to orbit the patient in a manner whereby the heads are always in closest proximity to the patient. Thus, the orbit is generally not circular. To accomplish this, means are provided for moving the heads towards and/or away from the central axis 22.

Means for moving the heads 13 and 14 towards and/or away from the central axis is shown by way of example as a motor means 28 and gear means 29 and 30 to effectively move the heads 13 and 14 along slots 31 and 32, respectively, to cause the heads to move away from or towards the central axis.

Power for the system is provided through power cable 31. The heads 13 and 14, of course, include the well known collimators and scintillators and photomultiplier arrays. The scintillators provide photons responsive to radiation emitting from the patient and striking the scintillator crystal. The photons are detected and amplified by the photomultipliers, not shown, to provide electrical data signals. The data signals are transferred to the control processor 33. The control processor also provides command signals which command the motor 23 to rotate the heads in a given direction and at a given speed. The control processor also provides command signals to the motor 28, for example.

Means, including wheels such as wheel 34, are provided for moving the patient table 16 having the patient bed 35 on which the patient 36 rests aligned with the central axis. The table moves along rails shown at 37. The means for moving the patient table 16 includes an electrical motor 30 and driving a gear means 39. The gear means 39 is attached, for example, to a drive mechanism which drives the wheels 38 of the table along the rails 37. The position of the table, of course, is controlled to obtain a slice of the portion of the patient's body desired. Thus, the control processor provides commands to the gantry 12 and receives data from the gantry. The data that is received is processed by the control processor in a well known manner to provide images on the imager 41.

It should be understood that while a system having two heads is described herein by way of example, a system having only one head or have more than two could also be used within the scope of the present invention.

In accordance with the invention, cableless couplings are provided between the power source, as indicated by power cable 31, the control processor 33 and the rotating portions of the gantry. These means in FIGS. 1 and 2 are illustrated by the slip rings 46, in this case comprising slip rings 47, 48 and 49 for coupling data, commands and power to the rotating portions of the gantry assembly.

Figure 2:
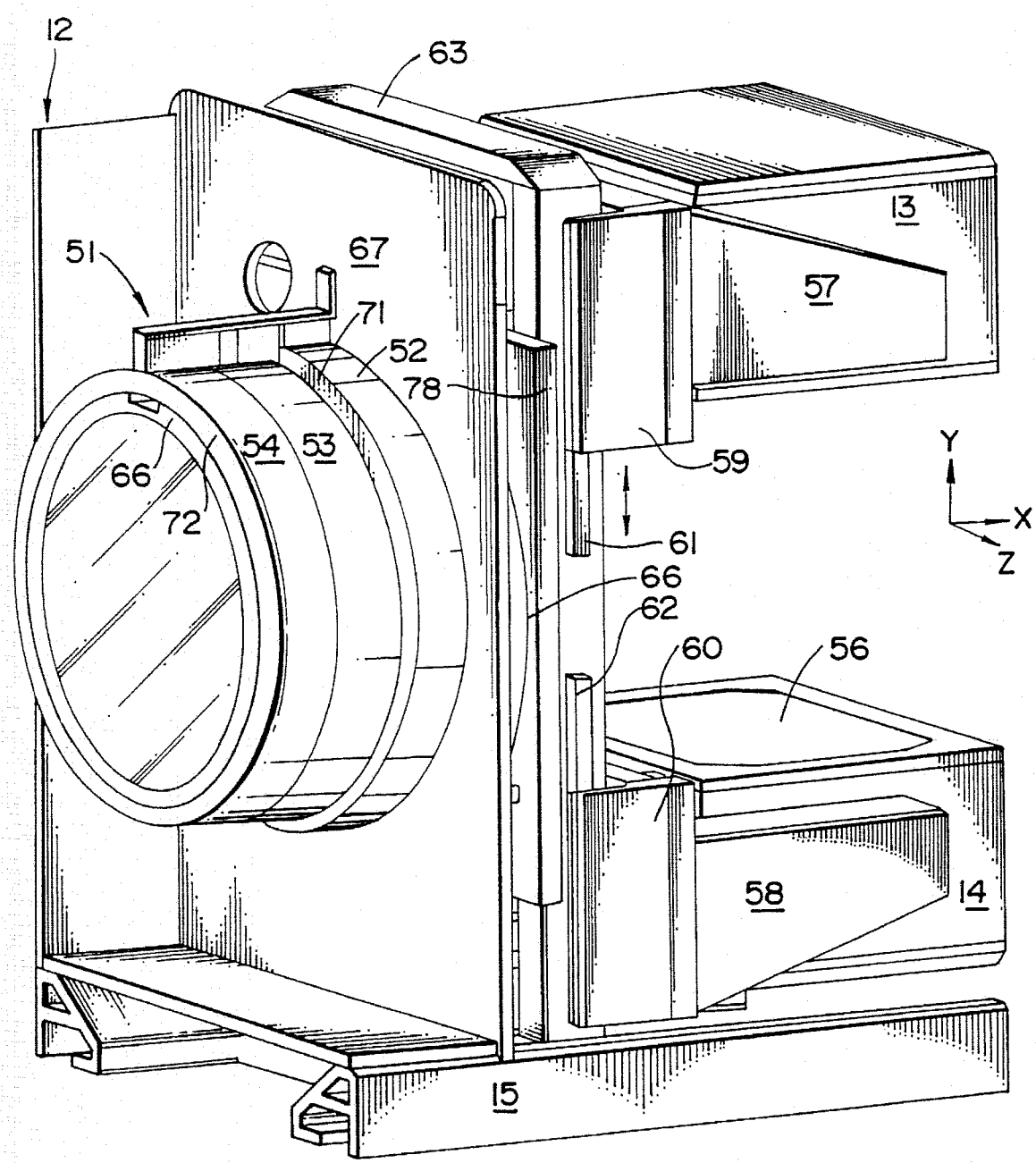
FIG. 2 shows in pictorial form a more detailed showing of the gamma camera unit utilizing a cableless coupling means, FIG. 3 a helical-like whole body scan.

In the drawings of FIGS. 1 and 2 the cableless means is shown in the form of the slip rings 46 and the brush assembly 51. The brush assembly 51 includes three brushes 52, 53 and 54 for use in coupling the power control and data signals between the sources of power and between the control processor and the rotating portions of the gantry.

Thus, power in the rotating portions of the gantry is required for the motor means 28 as well as for the photomultiplier arrays in the heads 13 and 14. The brushes utilized are by way of example the commercially available spring biased brushes of carbon or the like. The slip rings, by way of example, are commercially available slip rings.

FIG. 2 shows the embodiment of the gantry assembly that is coupled to the control processor and power source with slip rings and brushes. The gantry assembly 12, as shown in FIG. 2, includes the heads 13 and 14. The heads 13 and 14 include the collimators and camera such as schematically indicated at collimator 56 on head 14 in FIG. 2. The heads 13 and 14 are shown mounted through flanges 57 and 58 to the movable brackets 59 and 60. The movable brackets are moved by motor means 28 along rails 61 and 62. In place of rails, of course, other guidance means such as slots 31, 32 could be used. The rails are mounted to a rotating base 63. Rotating base 63 is mounted to rotate on bearings mounted between a cylindrical rotating component 66 and a vertical panel 67. The rotating cylinder has mounted thereon the plurality of slip rings such as slip rings 52, 53 and 54. The slip rings each have an outer-conductive layer mounted onto an insulating base such as base 71 shown, for example, as the insulating base for the slip ring 52.

The insulating base for slip ring 54 is shown at 72. The insulating bases rotate on a cylindrical means 66. In other words, the cylindrical rotating member 66 rotates on bearings in the panel 67. An auxiliary panel 78 which is effectively attached to the panel 67 so that the portions of the gantry assembly that rotate include the rotating base 63, the rotating cylindrical unit 66 and the pieces and parts of the gantry assembly that are mounted on either the cylinder 66 or the base 63. For example, the heads 13, 14 and components associated with the heads such as the flange 58 and the movable brackets 59 and 60 all rotate around the central axis 22.

Stationary, during rotation, are the parts of the brush assembly 51. Power and electrical conductors for conducting the command signals and the data signals are attached to the brush assembly. The photomultipliers in turn rotate with the rotating portions of the gantry such as the slip rings. Accordingly, there is no problem coupling power to the photomultipliers and/or the motor means 28 for moving the heads toward central axis or away from central axis.

While the gantry as shown in the drawings also includes the base 15, the gantry assembly could be made to move horizontally. However, in this exemplary embodiment, the bed is the moving portion for moving the patient to determine the cross section that is to be imaged and/or for providing whole body scans.

The embodiment of FIG. 3 schematically shows the inventive system being used to obtain a helical-like path 76 about the patient 77 for the camera head in a unique whole body scan. In operation then, the patient is placed on the patient table. The patient table is positioned between the heads 13 and 14 and alone the central axis 22 so that the cross section of the patient that is to be imaged will be imaged. The control processor then controls the rotating portion of the gantry and sends commands to the motor 23 to rotate the rotating parts of the gantry. The rotating parts of the gantry, include the heads which are thus rotated about the patient to describe an orbit that causes the heads to remain in close proximity to the patient throughout the scan. The output of the photomultiplier is sent to the control processor through the slip rings and the brushes whereby flexible cables and complicated cable assemblies for protecting the cables during rotation are not required. Also, the rotor of the gantry can continuously rotate in one direction. Thus, if a fast decaying radiation source is used, the heads can be checked with a slow orbit in a first rotating direction and if the orbit is all right then faster data acquisition rotation can be done. It is also possible with the use of the brushes and slip ring cableless coupling means to orbit the patient a number of times and to average the data and thereby provide improved signal-to-noise ratio.

The capability of orbiting a plurality of times also enables discarding data obtained during movement by the patient without requiring the patient to undergo another scan. The data acquired from the same views is also used to truly correct for motion instead of "approximately" correcting for motion.

While the invention has been described with reference to preferred embodiments, obvious modifications and alterations may occur to others upon reading and understanding the detailed description. However, it is intended that the invention be construed as including all such alterations and modifications insofar as they come within the scope of the appendent claims or the equivalents thereof.

What is claimed is:

1. A nuclear medicine diagnostic imaging system comprising:

a gantry assembly including a stationary gantry member having a central axis, a rotatable gantry member including a rotatable nuclear camera detector mounted on said rotatable gantry member for rotation about said central axis, patient support means aligned with said central axis, means for enabling said nuclear camera detector to continuously rotate about a patient on said patient support means during data acquisition, means for moving said patient support means during said data acquisition relative to said gantry assembly for causing the relative motion between said nuclear camera detector and said patient to describe a helix for providing a helical whole body scan, control processing means for supplying control signals for said system and for receiving data acquired by said nuclear camera detector responsive to said control signals and for processing said received data during said data acquisition to provide images of said patient, and said means for enabling said nuclear camera detector to continuously rotate about the patient including cableless coupling means for coupling electric power, control signals and radioactive emission data between said stationary gantry member and said nuclear camera detector.

2. The system of claim 1 wherein said cableless coupling means comprises a slip ring assembly including slip ring means and brush means.

3. The system of claim 1 wherein said helix has an elliptically shaped lateral cross section with the nuclear camera detector maintained at approximately the same distance from the patient throughout the scan.

4. A method for obtaining nuclear medicine diagnostic images using a gantry having a rotatable portion and a stationary portion, a nuclear camera detector on said rotatable portion, said nuclear camera detector on said rotatable portion being rotatable around a patient support means, said method comprising the steps of:

coupling electrical power, control signals and radioactive emission data between said rotatable portion and said stationary portion of said gantry in a manner enabling said rotatable portion to continuously rotate for more than two revolutions, administering radionuclide to a patient, continuously rotating said nuclear camera detector for a plurality of revolutions about said patient on said support means, longitudinally moving said patient's support means relative to said gantry assembly during said plurality of revolutions of said gantry for causing relative motion between said nuclear camera detector and said patient to describe a helix for providing a helical whole body scan, detecting radioactive energy emitted from said patient during said helical whole body scan, and processing the detected radioactive energy to provide image data of said patient during data acquisition.

5. The method of claim 4 wherein said helix has an elliptically shaped lateral cross section with the detector maintaining approximately the same distance from the patient throughout the scan.

6. A nuclear medicine diagnostic imaging system comprising: a gantry assembly including:

a stationary gantry member having a central axis, a rotatable gantry member including a rotatable nuclear camera detector mounted on said rotatable gantry member to continuously rotate said nuclear camera detector about said central axis, patient support means aligned with said central axis to have said nuclear camera detector continuously rotate about a patient on said patient support means, means for continuously moving said patient support means relative to said gantry assembly for causing the relative motion between said nuclear camera detector means and said patient to describe a helix for providing a helical whole body scan, control processing means for supplying control signals for said system and for receiving data acquired by said nuclear camera detector responsive to said control signals during said helical scan and for processing said received data during data acquisition to provide images of said patient, and cableless coupling means for coupling electric power, control signals and radioactive emission data between said stationary gantry member and said nuclear camera detector.

7. The nuclear medicine diagnostic imaging system of claim 6 wherein said helix has an elliptically shaped lateral cross section with the nuclear camera detector maintained at approximately the same distance from the patient throughout the scan.

8. The nuclear medicine diagnostic imaging system of claim 6 including means for moving said patient support means relative to said gantry assembly so that the rotating nuclear camera detector describes an elliptical plane about a section of the patient moved into position to be scanned whereby a tomographic image is obtained.

9. The nuclear medicine diagnostic imaging system of claim 6 wherein said cableless coupling means comprises inductive coupling means.

10. The nuclear medicine diagnostic imaging system of claim 6 wherein said cableless coupling means comprises optical coupling means.

11. The system of claim 6 wherein said cableless coupling means comprises a slip ring assembly including slip ring and brushes.

12. A method for obtaining nuclear medicine diagnostic images using a gantry having a rotatable portion and a stationary portion a nuclear camera detector on said rotatable portion, said method comprising the steps of:

administering radionuclide to a patient, continuously rotating said nuclear camera detector about said patient, providing movement of said patient relative to said gantry for causing relative longitudinal motion between said nuclear camera detector and said patient to describe a helix providing a helical whole body scan, and to enable selecting a portion of the patient to be covered by a tomographic scan, maintaining said continuous rotational motion about a single selected plane for at least 180 degrees of the patient whereby a tomographic image is obtained, and then continuing said helical whole body scan, detecting radioactive energy emitted from said patient during said scan, processing the detected radioactive energy, during data acquisition, to provide image data of said patient, and coupling electrical power, control signals and radioactive emission data between said rotating nuclear camera detector and said stationary portion of said gantry in a cableless manner enabling said rotatable nuclear camera detector to continuously rotate about the patient.

13. The method of claim 12 wherein said coupling step enabling said rotatable nuclear detector to continuously rotate about the patient comprises coupling said stationary portion and said rotatable portion using a slip ring assembly including a slip ring and a brush.

14. The method of claim 12 wherein said coupling step enabling said rotatable nuclear detector to continuously rotate about the patient comprises inductively coupling said stationary portion and said rotatable portion.

15. The method of claim 12 wherein said coupling step enabling said rotatable nuclear detector to continuously rotate about the patient comprises optically coupling said stationary portion and said rotatable portion.

16. A method for nuclear medicine diagnostic images using a gantry having a rotatable portion and a stationary portion, a patient support means, a nuclear camera detector on said rotatable portion, said nuclear camera detector on said rotatable portion being rotatable around the patient support means, said method comprising the steps of:

coupling electrical power control signals and radioactive emission data between said rotatable portion and said stationary portion on said gantry in a manner enabling said rotatable portion to continuously rotate, administering radionuclide to a patient, continuously rotating said nuclear camera detector in a plurality of revolutions about said patient on said patient support means;

longitudinally moving said patient support means relative to said gantry during the rotation of said gantry for causing the relative motion between said nuclear camera detector and said patient to describe a helix for providing a helical whole body scan, detecting radioactive energy emitted from said patient during said helical whole body scan, and processing the detected radioactive energy to provide image data of said patient, said processing step including:

reconstructing said data to obtain images, and beginning reconstruction during an early revolution of the nuclear camera detector about the patient and continuing during subsequent revolutions about the patient to provide evolving images.

17. A nuclear medicine diagnostic imaging system comprising:

a gantry assembly including a stationary gantry member having a central axis, a rotatable gantry member including a rotatable nuclear camera detector mounted on said rotatable gantry member for rotation about said central axis, a patient support aligned with said central axis, means for enabling said nuclear camera detector to continuously rotate about a patient on said patient support, means for moving said patient support means during data acquisition linearly relative to said gantry assembly causing the relative motion between said camera detector and said patient to describe a helix for providing a helical whole body scan, control processing means for supplying control signal data to said system, for receiving data acquired by said nuclear camera detector and for processing said received data during data acquisition to provide images of said patient, said control processing means including:

means for reconstructing said received data, said means for reconstructing beginning reconstruction during early revolutions of the camera detector about the patient and continuing during subsequent revolutions about the patient to provide evolving images, and said means for enabling said nuclear camera detector to continuously rotate about the patient including cableless coupling means for coupling electric power, control signals and radioactive emission data between said stationary gantry member and said nuclear camera detector.

18. A nuclear medicine diagnostic imaging system comprising a gantry assembly including:

a stationary gantry member having a central axis, a continuously rotatable gantry member including a nuclear gamma camera detector mounted on said rotatable gantry member to continuously rotate said gamma camera detector about said central axis, patient support means aligned with said central axis, means for enabling said nuclear camera detector to continuously rotate about a patient on said patient support means, means for continuously moving said patient support means longitudinally relative to said gantry assembly for causing the relative motion between said nuclear gamma detector means rotating about said patient and said longitudinally moving patient support means to describe a helix, for providing a helical scan, control processing means for supplying control signals to said system, for receiving data acquired by said nuclear camera detector responsive to said control signals during said helical scan and for processing said received data during data acquisition to provide images of said patient, said processing means processing said received data during the early revolutions of the camera detector about the patient and continuously processing said received data during subsequent revolutions about the patent to provide evolving images, and cableless coupling means for coupling electric power, said control signals and said received data between said stationary member and said nuclear camera detector to enable the continuous rotation of said gamma camera detector.

* * * * *